United States Patent [19]

Snyder et al.

[11] Patent Number: 4,828,980

[45] Date of Patent: May 9, 1989

[54] MEMBRANE STRUCTURE COATED WITH LOW PI PROTEIN OR CARBOHYDRATE AND METHODS OF MAKING AND USE

[75] Inventors: Brian A. Snyder, Rochester; Harold C. Warren, III, Rush; Roger W. Nelson, Fairport, all of N.Y.

[73] Assignee: Eastman Kodak Company, Rochester, N.Y.

[21] Appl. No.: 98,433

[22] Filed: Sep. 18, 1987

[51] Int. Cl.⁴ ................. G01N 33/546; G01N 33/569
[52] U.S. Cl. .................................. 435/7; 210/500.38;
427/244; 427/245; 428/315.5; 428/315.7;
428/315.9; 435/36; 436/529; 436/533; 436/534;
436/807; 436/824
[58] Field of Search ............... 436/529, 530, 531, 533,
436/534, 807, 824; 435/36, 7; 428/315.5, 315.7,
315.9; 210/500.38; 427/244, 245

[56] References Cited

U.S. PATENT DOCUMENTS

| | | | |
|---|---|---|---|
| 2,783,894 | 3/1957 | Lovell | 524/606 X |
| 3,825,410 | 7/1974 | Bagshawe | 23/230 |
| 3,888,629 | 6/1975 | Bagshawe | 23/230 |
| 4,066,512 | 1/1978 | Lai et al. | 195/127 |
| 4,092,116 | 5/1978 | Giaever | 435/7 X |
| 4,184,849 | 1/1980 | Cambiaso | 436/523 |
| 4,200,690 | 4/1980 | Root et al. | 435/7 |
| 4,407,943 | 10/1983 | Cole et al. | 435/7 |
| 4,414,324 | 11/1983 | Stout | 435/7 |
| 4,438,185 | 3/1984 | Taskier | 427/245 X |
| 4,459,361 | 7/1984 | Gefter | 436/534 |
| 4,692,417 | 9/1987 | Webster | 435/36 X |
| 4,702,840 | 10/1987 | Degen | 210/500.38 X |
| 4,707,266 | 11/1987 | Degen | 210/500.38 X |

OTHER PUBLICATIONS

*Meth. in Enzymology*, vol. XXV, 1972, pp. 531–536, Klapper, M. H. and Klotz, I. M. "Acylation with Dicarboxylic Acid Anhydrides".

Johnson et al, *Gene. Anal. Techn.* 1 (1984) pp. 3–8.

Primary Examiner—Sidney Marantz
Attorney, Agent, or Firm—J. Lanny Tucker

[57] ABSTRACT

A membrane structure useful in filtration and diagnostic tests includes a microporous membrane formed from a biologically inert material, such as a polyamide, and has a coating comprising one or more water-soluble proteins or carbohydrates. None of the proteins and carbohydrates in the coating has a pI greater than about 5. The membrane structure is prepared by contacting the microporous membrane with the appropriate protein or carbohydrate in an amount sufficient to provide a coating over the entire membrane surface without substantially diminishing the porosity of the membrane. The membrane structure is useful in various diagnostic test procedures, such as agglutination assays.

20 Claims, No Drawings

MEMBRANE STRUCTURE COATED WITH LOW PI PROTEIN OR CARBOHYDRATE AND METHODS OF MAKING AND USE

FIELD OF THE INVENTION

This invention relates to a membrane structure comprising a coated microporous membrane. It also relates to a method of making this membrane structure, and to a method of its use in agglutination methods.

BACKGROUND OF THE INVENTION

Microporous membranes have been used for separation of materials for a number of applications. Such materials can be prepared from a variety of inorganic or organic materials. For instance, polyamide microporous membranes have been used for agglutination assays because of their hydrophilicity and separation properties.

U.S. Pat. No. 4,066,512 (issued Jan. 3, 1978 to Lai et al) describes membrane structures composed of microporous membranes having a coating of a water-insoluble protein such as zein or collagen and methods of making such structures. Enzymes are bound to the protein coating in order to provide a large, stable catalytic surface for biological reactions. Useful materials for preparing microporous membranes include cellulose esters and polyamides such as nylon.

While polyamide materials are useful as microporous membranes in catalytic membrane structures as described above, they present problems when used in immunoassays involving the reaction of one immunoreactive species with its receptor. Nylon membranes, in particular, are highly susceptible to nonspecific interactions with immunoreactive species, such as antibodies and antigens. That is, the immunoreactive species are likely to complex with sites on the membrane instead of with, or in the absence of, corresponding receptor molecules. Thus, when such species are immobilized on solid carrier materials (for example, polymeric beads) which are placed near the membranes in agglutination assays, unwanted interactions arise between the membranes and the carriers. These undesired interactions cause background interference and a reduction in assay sensitivity. It would be highly desirable to have membranes which do not interfere with the activity of immunoreactive species.

The water-insoluble proteins described in U.S. Pat. No. 4,066,512 might be useful for reducing the undesirable interactions with immunoreactive species. However, those proteins require the use of organic solvents in coating procedures and therefore give rise to additional problems and concerns associated with organic solvents, such as objectionable odors, flammability and waste disposal. It would therefore be desirable to reduce or eliminate the interactions described above without the problems attendant with organic coating solvents.

SUMMARY OF THE INVENTION

The problems described above have been overcome with a membrane structure comprising a microporous membrane having an average pore size of less than about 10 micrometers, the membrane being formed from a biologically inert material and having a coating thereon comprising one or more water-soluble proteins or carbohydrates, none of which has a pI greater than about 5.

This invention also provides a method of preparing the membrane structure described above comprising (a) providing a microporous membrane formed from a biologically inert material and having an average pore size of less than about 10 micrometers, and (b) contacting the membrane with an aqueous solution comprising one or more water-soluble proteins or carbohydrates to provide a coating thereon, none of which proteins or carbohydrates has a pI greater than about 5, and the protein or carbohydrate being present in the solution in an amount sufficient to provide a coating over the entire membrane without substantially diminishing the porosity of the membrane.

Further, an agglutination method for the determination of a multivalent immunoreactive species in an aqueous liquid comprises:

(a) contacting the liquid with an agglutination reagent having associated therewith receptor molecules reactive with said species so as to form an agglutinate of the reaction product of the species and the receptor molecules, (b) simultaneously or subsequent to the contacting step (a), contacting the agglutinate with the membrane structure described above, (c) separating the agglutinate from unagglutinated materials, and (d) determining either the amount of agglutinate or unagglutinated materials.

The present invention provides membrane structures in which the nonspecific interactions of membrane with proteins or carrier materials is significantly reduced. This advantage is particularly important when the membrane structures are used in immunochemical reactions in which an immunoreactive species is caused to react with corresponding receptor molecules. As a result, the sensitivity of the immunochemical assays is greatly improved. The means for achieving these advantages is the pretreatment or coating of a microporous membrane with one or more water-soluble proteins or carbohydrates. None of the proteins or carbohydrates coated thereon has a pI greater than about 5.

The described proteins or carbohydrates provide a high density of negative charge on the membrane, which charge density repels negatively charged immunoreactive species. The results are improved complexation of species with receptor, reduced background and high sensitivity in assays. Furthermore, the problems associated with organic coating solvents needed for coating water-insoluble proteins are avoided. Only the types of proteins and carbohydrates described herein provide the unexpected results found in the practice of this invention.

The coating procedure used to prepare the membrane structures of this invention can be carried out in a matter of a few minutes, after which the membrane structure is ready for use. Alternatively, the structure can be dried and stored for an indefinite period of time without a loss in performance.

DETAILED DESCRIPTION OF THE INVENTION

In its broadest aspects, the present invention relates to a membrane structure which can be used for a variety of purposes, including filtration, chemical and biological catalysis, diagnostic tests, separations, immunosorptions and other uses readily apparent to one skilled in the art.

For example, such structures can be used for a sterilizing filtration of biological materials, filtration of hydraulic fluids and collection of bacteria or other organisms for water analysis. Alternatively, enzymes can be attached thereto and the resulting composite be used for biological catalysis as described in U.S. Pat. No. 4,066,512, noted above.

In a preferred embodiment, the structures are useful to detect and quantify any of a wide variety of immunoreactive species (mono- or multi-valent). Such species are generally antigens which have one or more sites for complexing with a corresponding receptor, that is, corresponding antibodies. Alternatively, the immunoreactive species to be detected can be an antibody which has one or more complexing sites reactive with the corresponding antigen or with an anti-antibody. Immunoreactive species which can be detected with this invention include, but are not limited to, Streptococcus A antigen, antigens from chlamydial and gonoccocal organisms, HTLV or HIV (human immunodeficiency viruses) or antibodies thereto, human chorionic gonadotropin (hCG), leutinizing hormone (LH), herpes viruses, drugs, antibiotics and other hormonal, bacterial or viral antigens and antibodies. In some instances, the species must be extracted from an organism or virus found in the biological specimen. Extraction procedures for a given species are known to one skilled in the art. Exemplary extraction procedures for Streptococcus A antigen are described below.

The microporous membrane useful in this invention is a thin porous material composed of any biologically inert material. Such materials do not interact with the immunoreactive species of interest or its receptor, and include materials, such as glass, ceramics, fibers, synthetic and natural polymers and others known in the art. Preferred materials are cellulose esters, polyamides and polyesters. The polyamides, such as nylons, are most preferred.

The membrane structure must have porosity sufficient for the intended use, whether it be filtration, assays or other likely uses. In the preferred embodiment of using the membrane structure in an agglutination assay, the porosity must be sufficient to allow fluids and unagglutinated materials to pass through but which will retain agglutinated materials. In other words, the membrane pores, after coating, must be large enough to allow passage of any reagents and unagglutinated particles, but not large enough to allow agglutinated particles to pass through. For use in an agglutination assay, the average membrane pore size is at least about 5 times, and preferably from about 6 to about 15 times the average diameter of the agglutination reagent used therein. More particularly, the average pore size of the membrane is generally less than about 10 micrometers, and preferably from about 0.2 to about 5 micrometers.

Useful membranes are commercially available from many sources. For example, useful polyamide materials are commercially available from Pall Corp. (Glen Cove, N.Y.). One useful membrane is a nylon-66 microporous membrane manufactured and marketed by that company as Biodyne A or Ultipor N-66. Useful cellulose acetate membranes are also commercially available. Useful membranes can be shaped to any desired configuration for a particular use.

As described above, the microporous membrane is coated prior to use with one or more water-soluble proteins or carbohydrates. Generally, only one protein or carbohydrate is coated thereon. However, not just any water-soluble protein or carbohydrate will provide the unexpected results obtained by the present invention. Rather, the materials useful herein, individually, do not have a pI greater than about 5.

The term pI (or isoelectric point) is known as the pH at which there is an equal number of positive and negative charges in a molecule so that the molecule is neutral in charge. The pI of a protein or carbohydrate can be measured using conventional materials and procedures. For example, it can be measured by isoelectric focusing using an LKB Ampholine PAG plate (available from LKB-Produkter AB, Bromma, Sweden), pH range 3.5–9.5, and standard calibrators.

Useful water-soluble proteins include casein derivatives or other protein derivatives which are negatively charged (for example, derivatives obtained from acylation, alkylation or sulfonation of casein, such as succinylated casein, succinylated bovine serum albumin, and succinylated collagen and other negatively charged proteins or carbohydrates readily apparent to one skilled in the art). These materials are readily prepared by acylating, alkylating or sulfonating a protein having available amine groups using suitable conditions. Useful acylating agents include, but are not limited to, those described in U.S. Pat. No. 4,591,571 (issued May 27, 1986 to Kuboyama et al), such as anhydrides, acyl halides and esters derived from dicarboxylic and polycarboxylic acids. Succinic anhydride is a preferred acylating agent. The preparation of succinylated casein is described below in Example 3.

Alkylating and sulfonylating agents useful in modifying the proteins for use in this invention include, but are not limited to bromoacetic acid, chloroacetic acid, fluoronitrobenzene, m-(chlorosulfonyl)benzoic acid, bromomalonic acid, bromopropionic acid and p-(chlorosulfonyl)benzoic acid.

Useful carbohydrates include water-soluble cellulose derivatives. Representative compounds are carboxymethyl cellulose, carboxyethyl cellulose and others which would be readily apparent to one skilled in the art. These cellulose derivatives are usually commercially available.

Preferred coating materials include succinylated casein, carboxymethyl cellulose, succinylated bovine serum albumin and succinylated collagen. Succinylated casein is most preferred.

The membrane structure can be prepared by contacting a microporous membrane of desired configuration with an aqueous solution of the appropriate proteins or carbohydrates by allowing a solution of the protein or carbohydrate to flow through the membrane at room temperature. In some cases, heating the solution up to 40° C. for several minutes may be useful. The total protein or carbohydrate present in the solution is an amount sufficient to provide a coating over the entire membrane without substantially diminishing the porosity of the membrane. In other words, the coating should completely cover the surface of the membrane, but be thin enough so that the pores of the membrane are not blocked to an undesirable extent. At least 50% of the original porosity of the membrane prior to coating should be retained after coating. The amount of protein or carbohydrate needed to achieve these results can be varied depending upon the membrane porosity, solution viscosity and average pore size, but it is generally an amount sufficient to coat the membrane with at least about 25 $\mu g/cm^2$ of membrane surface. Very little of the protein or carbohydrate is left in the coating solution after membrane coating.

The coated membrane structure can be used immediately in its wet state. However, it can also be dried for storage and later use. Any suitable drying technique can be used as long as the coating is not adversely affected.

While the membrane structures of this invention can be used in a number of ways, it is preferred that they be used to detect a multivalent immunoreactive species, such as Streptococcus A antigen. This embodiment of the invention relating to Streptococcus A antigen is presented for illustrative purposes, but it will be understood that the scope of the invention is not so limited.

A biological sample suspected of containing the Streptococcus A organism can be collected from a patient in any suitable manner. However, generally an applicator means is used to collect a biological sample by contacting the area of suspected infection with the applicator swab thereby collecting cells of Streptococcus A if they are present. Subsequently, the antigens are extracted from the organisms in a suitable manner. A preferred extraction procedure includes dipping the swab in a suitable extraction composition containing one or more reagents which singly or in combination cause release of the Streptococcus A antigen from the organism, specimen cells and other debris in the sample.

Useful extraction compositions known in the art include a mixture of nitrite salt and glacial acetic acid, as described in E.P. Publication 150,567, and enzymes derived from the bacterium *Streptomyces albus* as described in U.S. Pat. No. 4,618,576 (issued Oct. 21, 1986 to Rosenstein et al).

A preferred extraction composition is a mixture of a nitrite salt (for example, sodium nitrite or potassium nitrite) with a nonvolatile organic acid (for example, succinic or citric acid) as described in copending and commonly assigned U.S. Ser. No. 098,431, filed on even date herewith by Snyder et al and entitled "Kit for Extracting Streptococcus A Antigen and a Method of Using Extracted Antigen", now abandoned in favor of continuation-in-part U.S. Application Ser. No. 131,618 filed Dec. 11, 1987.

Extraction can be accompanied by incubation for a short period of time if desired. Centrifugation can also be used to remove extraneous material. After extraction, the medium containing the extracted antigen can be neutralized if necessary to bring the medium pH to that appropriate for antigen-antibody reaction. Such optional steps are noted, for example, by Slifkin et al, *J. Clin. Microbiol.* 15(1), pp. 187–189, 1982.

The presence of a multivalent immunoreactive species, for example, Streptococcus A antigen, is detected by an agglutination reagent which comprises water-insoluble particles having receptor molecules (for example, antibodies to Streptococcus A antigen) reactive with the species bound in a suitable manner to the surface of the particles. Reaction (or binding) between immunoreactive species and receptor then results in a linking together of the particles so that they form large agglutinates.

The amount of species can be detected by either measuring the amount of agglutinate or the amount of unagglutinated materials. The detection can be carried out in any suitable manner readily apparent to one skilled in the art, for example, by visually observing the amount of agglutinate. Preferably, tracer molecules are used in association with the particles, as described in detail below.

Suitable particles useful in the indicator reagent can be natural or synthetic particles which are water-insoluble and capable of having a suitable number of tracer molecules associated therewith in some manner. Examples of useful particles include ferritin crystals, agarose particles, glass beads, polymeric particles, such as latex particles, and others known in the art. The following references describe representative useful particles: U.S. Pat. Nos. 3,700,609 (issued Oct. 24, 1972 to Tregear et al), 3,853,987 (issued Dec. 10, 1974 to Dreyer), 4,108,972 (issued Aug. 22, 1978 to Dreyer), 4,258,001 (issued Mar. 24, 1981 to Pierce et al), 4,401,765 (issued Aug. 30, 1983 to Craig et al), 4,419,453 (issued Dec. 6, 1983 to Dorman et al), 4,459,361 (issued July 10, 1984 to Gefter), 4,478,946 (issued Oct. 23, 1984 to Van der Merwe) and 4,591,571 (issued May 27, 1986 to Kuboyama et al). The particles useful in an agglutination assay are generally quite small, that is less than about 2 micrometers in diameter. Preferably, they have an average diameter of from about 0.1 to about 1 micrometer.

Particularly useful particles are polymeric latex particles, and more preferably they are what are known in the art as core-shell polymeric latex particles. A wide variety of monomers can be used in the preparation of such particles as long as the particles are water-insoluble. A worker skilled in the polymer chemistry art would be able to design and prepare suitable latex particles. Preferred core-shell polymeric latex particles used in the practice of this invention are described in Example 2 below. These particles have a core composed of homo- or copolymers of styrene, and a shell composed of homo- or copolymers of chloromethylstyrene.

The particles useful in the practice of this invention preferably have sufficient tracer molecules associated therewith in order to allow quantitative determination of the species from the amount of tracer seen in either the agglutinate or in the unagglutinated materials. The tracer molecules can be suitably attached to the outer surface of the particles, or preferably, distributed within the particles. Any tracer material which allows detection of the agglutinate can be used. If ferritin cyrstals are used as the particles, the tracer molecules are molecules of iron inherently in those crystals. Other natural or synthetic particles can have, as tracers: radioisotopes, colorimetric dyes, fluorescent compounds, chemiluminescent compounds, phosphorescent compounds and other detectable materials known in the art. Preferably, the tracer is a radioisotope, colorimetric dye or fluorescent compound [for example, a fluorescent dye or rare earth chelate, as described for example, in U.S. Pat. No. 4,259,313 (issued Mar. 31, 1981 to Frank et al)]. Most preferably, the tracer is a colorimetric dye. A worker skilled in the art would be able to combine an appropriate tracer with the particular particle used.

The tracer can be distributed within the particles in any suitable manner. For example, the tracer can be uniformly distributed therein as shown for example in U.S. Pat. No. 3,853,987 (noted above). Preferably, the tracer molecules are located in a restricted area of the particles, for example, near the surface or predominantly in the interior thereof. In the preferred core-shell particles, the tracer can be in either the core or shell, but most preferably, it is substantially in the core of the particles. In other words, very little (for example, less than 5% by weight) of the dye is in the shell portion of the particles.

Receptor molecules (for example, antibodies) reactive to the immunoreactive species to be detected (such as Streptococcus A antigen) are bound to the outer surfaces of the particles in a suitable manner, for example by adsorption or covalent attachment. Attachment can be achieved using known techniques, as described for example in the references cited above. Covalent attachment is preferred. When the receptor molecules are antibodies, either monoclonal or polyclonal antibodies can be used. Antibodies (whole or fragments thereof) can be obtained commercially or prepared using known techniques.

Simultaneously or subsequent to contact of extracted immunoreactive species with receptor molecules to form the agglutinate, the agglutinate is also contacted with the water-insoluble membrane structure of this invention. In one embodiment, the agglutinate can be formed in a separate container and then brought into contact with the membrane structure. Alternatively and preferably, the agglutinate is formed in the presence of the membrane structure, for example as mounted in a test device in which the assay is carried out.

A suitable incubation period can be used to optimize agglutination, if desired, before or during contact with the membrane. After that period, unagglutinated residual materials are washed through the membrane while leaving the agglutinate thereon. Any suitable wash fluid can be used in this step, but preferably the wash solution has a pH of from about 5 to about 10 and contains an ionic compound, such as a salt. Details regarding this preferred wash solution are provided in copending and commonly assigned U.S. Ser. No. 19,850, filed Feb. 27, 1987 by Snyder et al.

Once the unagglutinated residual materials have been washed through the membrane, the amount of immunoreactive species in either the agglutinate or unagglutinated materials can generally be determined with the unaided eye if the tracer is a readily visible colorimetric dye. Otherwise, standard colorimetric detection equipment can be used. Other types of tracers, for example, radioisotopes, fluorescent dyes, phosphorescent dyes, and the like, require suitable detection equipment.

While the present invention is not so limited, an assay for an immunoreactive species can be carried out using a suitable test device which comprises the membrane structure of the present invention. Such a device can have one or more wells into which extracted antigen is deposited for reaction with the agglutination reagent. This reagent can be added to the device during the assay, or incorporated therein at the time of manufacture. Once the agglutinate is formed, the unagglutinated materials can be washed through the membrane into a separate compartment below the membrane. An example of such a test device is described and claimed in copending and commonly assigned U.S. Ser. No. 19,810 filed Feb. 27, 1987 by Hinckley. Other variations of useful test devices would be within the purview of an ordinary worker skilled in the art.

In the examples which follow, illustrating the practice of this invention, the materials used were obtained as follows:

bovine serum albumin, zein, collagen and casein (#C5890) from Sigma Chemical Co. (St. Louis, Mo.),
nylon-66 membranes from Pall Corp. (Glen Cove, N.Y.),
Oil Red EGN dye from Aldrich Chemical Co. (Milwaukee, Wis.),
carboxymethyl cellulose, types 7M and 7MI, from Hercules Co. (Wilmington, Del.),
monoclonal antibodies to Streptococcus A antigen were obtained from Streptococcus A vaccine according to the procedure described by McCarty et al, J. Exp. Med., 102, 11, 1955, and
the remainder either from Eastman Kodak Company (Rochester, N.Y.) or prepared using standard procedures and readily available starting materials.

Succinylated casein was prepared by the procedure described in Example 2 below.

Succinylated bovine serum albumin was prepared by adding bovine serum albumin (200 mg) to 0.5 molar sodium phosphate buffer (10 ml, pH 8.5). Succinic anhydride (200 mg) was then added, and the resulting mixture was stirred at 25° C. for three hous. The mixture was dialyzed against distilled water using Spectrapor 2 dialysis tubing (Spectrum Medical Industries, Inc., Los Angeles, Calif.). There was obtained 12 ml of product containing 1.6% solids. Sodium azide (0.01%) was added as a preservative.

Succinylated collagen was prepared by a method similar to that described for preparing succinylated bovine serum albumin to obtain 20 ml of product (1% solids).

EXAMPLE 1

Membrane Structure Treated with Carboxymethyl Cellulose

This example shows the preparation of a membrane structure using carboxymethyl cellulose.

Antibodies to Streptococcus A antigen were adsorbed to $0.8\mu$ polystyrene beads into which europium (III) (thenoyltrifluoroacetone)$_3$ chelate had been imbibed, by mixing the beads and antibodies end-to-end for about two hours. The amount of antibody thereby attached was 5% based on bead weight. An aqueous solution (0.3% solids) of the resulting agglutination reagent was added to nylon-66 microporous membranes (5 $\mu$m average pore size) which had been pretreated with each of: (1) 0.75% casein, (2) 2% 7M carboxymethyl cellulose, and (3) 2% 7MI carboxymethyl cellulose. The reagent was then washed with a buffered solution (pH 8) of sodium chloride (200 $\mu$l, 1 molar salt). The background levels were then determined by measuring the amount of surface fluorescence (excitation 342 nm, emission 612 nm) remaining on the filter after the wash step. This fluorescence value is a measure of the background, that is, a measure of the interactions between the membrane structure and agglutination reagent. The lower the fluorescence value, the lower the background.

Table I below lists the results of background fluorescence. It is apparent that carboxy-methyl cellulose substantially reduced the background compared to casein.

TABLE I

| Membrane (Treatment) | Background Fluorescence on Filter |
|---|---|
| Nylon (casein) | 844 |
| Nylon (carboxymethyl cellulose, 7M) | 252 |
| Nylon (carboxymethyl cellulose, 7MI) | 394 |
| Example 2: Membrane Structure Prepared with Succinylated Casein and Its Use in an Assay for *Streptococcus A Antigen* | |

This example is similar to Example 1 except that the membrane structure, was treated with succinylated casein.

Succinylated casein was prepared in the following manner: casein (50 g) was added to 0.5 molar sodium phosphate, dibasic (2.5 liters, pH 8.5). The resulting mixture was heated to 40° C. with stirring to complete dissolution. After the heat was removed, succinic anhydride (50 g) was added to the mixture, followed by incubation under continuous stirring for three hours at ambient temperature. The resulting solution was defiltered through a 1000 molecular weight cutoff membrane (available as OK-PS from Osmonics, Inc., Minnetonka, Minn.). The initial resistivity of the effluent was 17.5 milliohms. After about 8 turnovers, the resistivity had dropped to 1.7 milliohms. The solution was then collected and diluted with deionized water to 2% solids.

A membrane structure was prepared by coating a nylon-66 microporous membrane with a succinylated casein solution (50 μl) containing 2% solids.

Antibodies to Streptococcus A antigen were covalently immobilized on core-shell polymeric particles composed of poly(styrene-co-2-acetoace-toxyethyl methacrylate) (70:30) in the core and poly-(m,p-chloromethylstyrene) in the shell to provide an agglutination reagent. The average diameter of the particles was about 0.45 micrometer. These particles contained a red dye (Oil Red EGN) in the core prepared according to the teachings of Belgian Pat. No. 843,647.

A solution of succinic anhydride (10 mg/ml dimethyl sulfoxide) was added to a suspension of the agglutination reagent described above at a weight ratio of 1 part anhydride to 1 part total protein. The resulting suspension was mixed for four hours at 25° C., centrifuged for 5 minutes at 7000 rpm and the resulting pellet was resuspended in 0.1 molar glycine buffer (pH 8.5) to a concentration of 0.3% solids.

The agglutination reagent was then mixed with Streptococcus A antigen obtained from a biological sample and incubated for two minutes at 37° C. Background controls were obtained by incubating the reagent in an extraction solution without antigen. Samples of the agglutinate (150 μl) were then placed on a membrane structure prepared with succinylated casein, as described above, and a second structure prepared with casein.

The agglutinate on the membrane structures were then washed with 1 molar tricine (200 μl, pH 8.6) to remove unagglutinated materials.

The amount of agglutinate remaining on the membrane structures was then evaluated by measuring the surface reflectance (at 530 nm) of the dye in the agglutinate and converting to $D_T$ (transmission density) using the Williams-Clapper transform (*J. Opt. Soc. Am.*, 43, p. 595, 1953). The background levels were determined to be 0.125 for the succinylated casein membrane structure and 0.194 for the casein membrane structure. It is apparent that the succinylated casein provides a significant reduction in background over casein. The signal level of agglutinate on the succinylated casein treated structure was 0.445, and the signal for the casein treated structure was similar to that of succinylated casein. The background signal for a nylon-66 microporous membrane which was untreated was greater than 0.500, which is comparable to the signal of the agglutinate itself.

The structure treated with succinylated casein exhibited significantly reduced background and the agglutinate signal remained strong. This structure was found to exhibit high stability for long term storage.

EXAMPLE 3

Comparison Example

This example compares membrane structures of the present invention with a structure similarly prepared using zein as the coating material as described in U.S. Pat. No. 4,066,512, noted above.

Assays for Streptococcus A were carried out as follows: a microporous membrane (5 μm BIODYNE A membrane from Pall Corp.) was incorporated into a disposable device. About 40 μl of a 1% sodium phosphate solution of each of succinylated casein, succinylated bovine serum albumin, succinylated collagen or zein was added to the device, followed by addition of 40 μl of a 1 molar sodium chloride solution. A suspension of core-shell beads composed of a core of poly(styrene-co-acetoacetoxyethyl acrylate) (85:15) and a shell of poly (m and p-chloromethyls-tyrene-co-methacrylic acid (99.8:0.2), which had been imbibed with 3% acetonitrile solution of Oil Red EGN dye was then added. The bead composition was in glycine buffer solution (pH 8.5) and contained 0.3% solids. Streptococcus A antigen (40 μl), which had been extracted by the method described in copending and commonly assigned U.S. Ser. No. 131,618 of Snyder et al, noted above which is a continuation-in-part of U.S. Ser. No. 098,431 (now abandoned), was then added. This mixture was incubated for 2 minutes at 37° C., then the solution was allowed to drain through the membrane. A wash solution of 1 molar sodium chloride (90 μl) was added. The dye obtained from the agglutinated beads on the membrane was measured by surface reflectance. Reflectance readings were converted to transmission values using the Williams-Clapper transform, which values are shown in Table II below.

A similar Streptococcus A assay was also run using a membrane treated with bovine serum albumin and beads containing a fluorescent europium chelate as described in U.S. Pat. No. 4,259,313, noted above. Results of this test showed that the bovine serum albumin coating did not reduce background.

TABLE II

| Membrane Treatment | Strep A Antigen (mg) $D_T$ | | |
|---|---|---|---|
| | (Background) 0 | 12.4 | 266 |
| succinylated casein | 0.020 | 0.035 | 0.151 |
| succinylated bovine serum albumin | 0.074 | 0.138 | 0.187 |
| succinylated collagen | 0.023 | 0.037 | 0.119 |
| zein | 0.187 | 0.244 | 0.213 |

Results of these tests show the following: bovine serum albumin and zein do not reduce background. There was an improvement obtained with succinylated bovine serum albumin, but not as much as was obtained with succinylated casein. Unsuccinylated collagen was too viscous to use because it blocked membrane pores, however, background reduction obtained with succinylated collagen was similar to that obtained with succinylated casein.

The invention has been described in detail with particular reference to preferred embodiments thereof, but it will be understood that variations and modifications can be effected within the spirit and scope of the invention.

We claim:

1. A membrane structure comprising a microporous membrane having an average pore size of less than about 10 micrometers, said membrane being formed from a biologically inert material and having a coating directly thereon comprising one or more water-soluble proteins or carbohydrates, none of which has a pI greater than about 5.

2. The membrane structure of claim 1 wherein said membrane has an average pore size of from about 0.2 to about 5 micrometers.

3. The membrane structure of claim 1 wherein said biologically inert material is a polyamide.

4. The membrane structure of claim 3 wherein said biologically inert material is nylon.

5. The membrane structure of claim 1 wherein said water-soluble protein or carbohydrate is succinylated casein, carboxymethyl cellulose, succinylated bovine serum albumin or succinylated collagen.

6. The membrane structure of claim 5 wherein said water-soluble protein is succinylated casein.

7. A method of preparing a membrane structure comprising
   (a) providing a microporous membrane formed from a biologically inert material and having an average pore size of less than about 10 micrometers, and
   (b) contacting said membrane with a solution comprising one or more water-soluble proteins or carbohydrates to provide a coating directly thereon, none of which proteins or carbohydrates has a pI greater than about 5, and said protein or carbohydrate being present in the solution in an amount sufficient to provide a coating over the entire membrane without substantially diminishing the porosity of said membrane.

8. The method of claim 7 further comprising the step of drying said coating.

9. The method of claim 7 wherein said protein or carbohydrate is coated in an amount of at least about 25 μg/cm² of membrane surface.

10. The method of claim 7 wherein said water-soluble protein or carbohydrate is succinylated casein, carboxymethyl cellulose, succinylated bovine serum albumin or succinylated collagen.

11. The method of claim 10 wherein said water-soluble protein is succinylated casein.

12. The method of claim 7 wherein said biologically inert material is a polyamide.

13. The method of claim 12 wherein said biologically inert material is nylon.

14. An agglutination method for the determination of a multivalent immune species in an aqueous liquid comprising:
   (a) contacting said liquid with an agglutination reagent having associated therewith receptor molecules reactive with said multivalent immune species so as to form an agglutinate of the reaction product of said multivalent immune species and said receptor molecules,
   (b) simultaneously or subsequent to said contacting step (a), contacting said agglutinate with a membrane structure comprising a microporous membrane formed from a biologically inert material, having an average pore size of less than about 10 micrometers and having a coating directly thereon comprising one or more water-soluble proteins or carbohydrates, none of which has a pI greater than about 5,
   (c) separating said agglutinate from unagglutinated materials, and
   (d) determining either the amount of agglutinate or unagglutinated materials.

15. The method of claim 14 wherein said agglutination reagent has tracer molecules associated therewith.

16. The method of claim 15 wherein said tracer molecules present in the agglutinate are determined in step (d).

17. An agglutination method for the determination of Streptococcus A antigen in an aqueous liquid comprising:
   (a) contacting said liquid with an agglutination reagent having associated therewith both antibody molecules for Streptococcus A antigen and tracer molecules, so as to form an agglutinate of the reaction product of said antigen and said antibody molecules,
   (b) simultaneously or subsequent to said contacting step (a), contacting said agglutinate with a membrane structure comprising a microporous membrane formed from nylon, having an average pore size of less than about 10 micrometers, and having a coating directly thereon of succinylated casein,
   (c) separating said agglutinate from unagglutinated materials, and
   (d) determining the tracer in either the agglutinate or unagglutinated materials.

18. The method of claim 17 wherein said tracer is determined in said agglutinate.

19. The method of claim 17 wherein said agglutination reagent comprises water-insoluble core-shell polymeric particles having substantially all of said tracer molecules in said particle cores.

20. The method of claim 17 wherein said tracer is a colorimetric dye.

* * * * *

UNITED STATES PATENT AND TRADEMARK OFFICE
CERTIFICATE OF CORRECTION

PATENT NO. : 4,828,980

DATED : Issued May 9, 1989

INVENTOR(S) : Brian A. Snyder; Harold C. Warren, III and Roger W. Nelson

It is certified that error appears in the above-identified patent and that said Letters Patent is hereby corrected as shown below:

Column 10, line 47, delete "Strep A Antigen (mg)" and substitute therefor -- Strep A Antigen (ng) --.

Signed and Sealed this

Twentieth Day of March, 1990

Attest:

JEFFREY M. SAMUELS

*Attesting Officer*   *Acting Commissioner of Patents and Trademarks*